US009499448B2

(12) United States Patent
Thorpe et al.

(10) Patent No.: US 9,499,448 B2
(45) Date of Patent: Nov. 22, 2016

(54) MICROBIAL COMPOSITION COMPRISING LIQUID FERTILIZER AND PROCESSES FOR AGRICULTURAL USE

(71) Applicant: Agrinos AS, Lysaker (NO)

(72) Inventors: Darrell T. Thorpe, Eustis, FL (US); Jaime López-Cervantes, Obregon (MX)

(73) Assignee: Agrinos AS, Lysaker (NO)

( * ) Notice: Subject to any disclaimer, the term of this patent is extended or adjusted under 35 U.S.C. 154(b) by 0 days.

(21) Appl. No.: 14/700,848

(22) Filed: Apr. 30, 2015

(65) Prior Publication Data
US 2015/0307408 A1 Oct. 29, 2015

Related U.S. Application Data

(63) Continuation of application No. 13/829,300, filed on Mar. 14, 2013, now abandoned.

(60) Provisional application No. 61/616,306, filed on Mar. 27, 2012, provisional application No. 61/616,872, filed on Mar. 28, 2012, provisional application No. 61/616,928, filed on Mar. 28, 2012.

(51) Int. Cl.
| | | |
|---|---|---|
| C12N 1/14 | (2006.01) | |
| C05F 11/08 | (2006.01) | |
| C05C 11/00 | (2006.01) | |
| C05C 9/00 | (2006.01) | |
| A01N 63/02 | (2006.01) | |
| C05C 3/00 | (2006.01) | |
| C12N 1/20 | (2006.01) | |
| C12R 1/00 | (2006.01) | |

(52) U.S. Cl.
CPC ............... *C05F 11/08* (2013.01); *A01N 63/02* (2013.01); *C05C 3/00* (2013.01); *C05C 9/00* (2013.01); *C05C 11/00* (2013.01); *C12N 1/14* (2013.01); *C12N 1/20* (2013.01); *C12R 1/00* (2013.01)

(58) Field of Classification Search
None
See application file for complete search history.

(56) References Cited

U.S. PATENT DOCUMENTS

| | | |
|---|---|---|
| 4,536,207 A | 8/1985 | McCandliss |
| 4,812,159 A | 3/1989 | Freepons |
| 4,952,229 A | 8/1990 | Muir |
| 4,964,894 A | 10/1990 | Freepons |
| 4,978,381 A | 12/1990 | Hadwiger |
| 5,266,096 A | 11/1993 | Slavensky |
| 5,374,627 A | 12/1994 | Ito et al. |
| 5,733,851 A | 3/1998 | Villanueva |
| 5,998,173 A | 12/1999 | Haynes et al. |
| 6,060,429 A | 5/2000 | Ben-Shalom |
| 6,232,270 B1 | 5/2001 | Branly |
| 6,407,040 B1 | 6/2002 | Nichols |
| 6,524,998 B1 | 2/2003 | Kloepper et al. |
| 6,649,566 B2 | 11/2003 | Doostar |
| 6,979,664 B1 | 12/2005 | Smith et al. |
| 7,241,463 B2 | 7/2007 | Nielsen |
| 7,250,068 B1 | 7/2007 | Smith et al. |
| 8,748,124 B2 | 6/2014 | López-Cervantes et al. |
| 9,253,989 B2 | 2/2016 | Smith et al. |
| 2008/0257000 A1 | 10/2008 | McMahon et al. |
| 2009/0120147 A1 | 5/2009 | Blais |
| 2010/0267999 A1 | 10/2010 | Lau et al. |
| 2012/0084886 A1 | 4/2012 | López-Cervantes et al. |
| 2012/0329135 A1 | 12/2012 | López-Cervantes |
| 2015/0257393 A1 | 9/2015 | Nijak et al. |

FOREIGN PATENT DOCUMENTS

| | | |
|---|---|---|
| JP | 2003160420 | 6/2003 |
| KR | 20050117990 | 12/2005 |
| WO | WO 89/01288 | 2/1989 |
| WO | WO 2011/157747 | 12/2011 |
| WO | WO 2012/175739 | 12/2012 |

OTHER PUBLICATIONS

Aye et al. "Improved chitin production by pretreatment of shrimp shells," *J. of Chem. Tech and Biotech.*, vol. 79, pp. 421-425, 2004.
Bhaskar et al. "Shrimp biowaste fermentation with Pediococcus acidolactici CFR2182: Optimization of fermentation conditions by response surface methodology and effect of optimized conditions on deproteineation/demineneralization and carotenoid recovery," *Enzyme and Microbial Tech.* vol. 40, pp. 1427-1434, 2007.
Bhattacharya et al. "Bacterial Chitinases: Properties and Potential," *Grit. Reviews in Biotech.*, vol. 27, pp. 21-28, 2007.
Campbell et al. "A Study of Chitin-decomposing Micro-organisms of Marine Origin," *J. Gen. Microbial.*, vol. 5, pp. 894-905, 1951.
Cira et al. "Pilot scale lactic acid fermentation of shrimp wastes for chitin recovery," *Process Biochemistry*, vol. 37, pp. 1359-1366, 2002.
Cody, "Distribution of Chitinase and Chitobiase in Bacillus," *Current Micro.*, vol. 19, pp. 201-205, 1989.
Lopez-Cervantes et al., "Analysis of free amino acids in fermented shrimp waste by high-performance liquid chromatography," *Journal of Chromatography*, vol. 1105, No. 1-2, pp. 106-110, 2006.
Nandakumar, et al. "Chitinolytic Activity of Native *Pseudomonas fluorescens* Strains," *J. Agric. Sci. Technol.*, vol. 9, pp. 61-68, 2007.
Sini et al. "Study on the production of chitin and chitosan from shrimp shell by using Bacillus subtilis fermentation," *Carbohydrate Res.*, vol. 342, pp. 2423-2429, 2007.

*Primary Examiner* — Robert Yamasaki
*Assistant Examiner* — Teresa E Knight
(74) *Attorney, Agent, or Firm* — Klarquist Sparkman, LLP

(57) ABSTRACT

Processes and compositions are disclosed that enhance crop production, increase plant defensive processes and/or decrease the level of plant pathogens. The compositions comprise a microbial composition and liquid fertilizer, preferably a liquid fertilizer that contains at least soluble nitrogen. The composition can be applied immediately to soil, foliage, seeds or seedlings. Alternatively, the composition may be activated by incubation for up to about seven days to form an activated composition. The incubation conditions influence the properties of the consortium after incubation. In one embodiment, the compositions comprise one or more lactic acid producing bacteria, one or more nitrogen fixing bacteria, and liquid fertilizer comprising soluble nitrogen. In preferred embodiments, there are multiple genera and/or species of lactic acid bacteria and nitrogen fixing bacteria. In a particularly preferred embodiment, the composition comprises HYTa in liquid fertilizer.

12 Claims, 1 Drawing Sheet

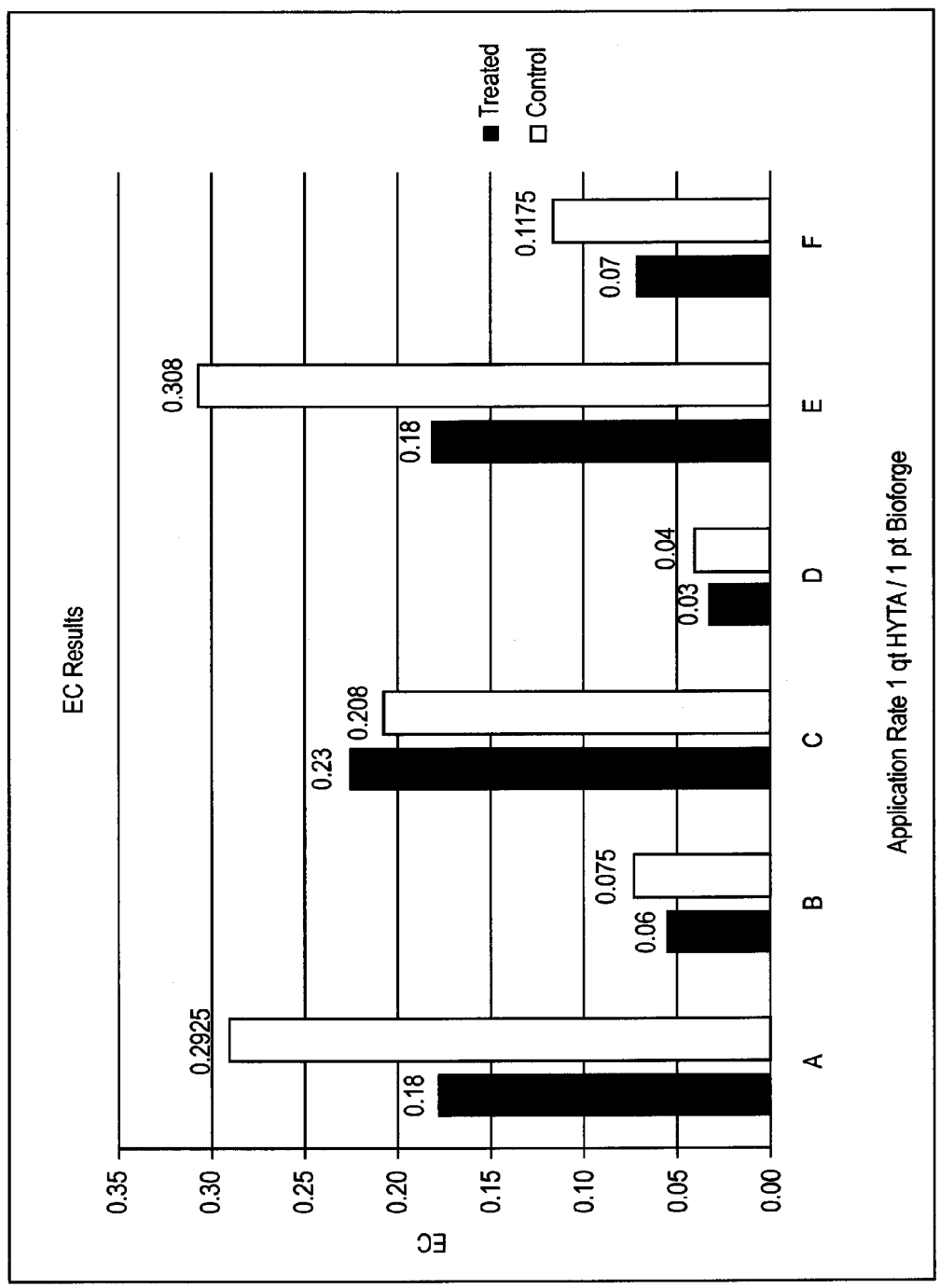

MICROBIAL COMPOSITION COMPRISING LIQUID FERTILIZER AND PROCESSES FOR AGRICULTURAL USE

CROSS REFERENCE TO RELATED APPLICATIONS

This application is a continuation of co-pending U.S. application Ser. No. 13/829,300, filed Mar. 14, 2013, which in turn claims the benefit under 35 U.S.C. §119 of U.S. Provisional Application Ser. Nos. 61/616,928, filed Mar. 28, 2012; 61/616,872, filed Mar. 28, 2012; and 61/616,306, filed Mar. 27, 2012, all of which are incorporated herein in their entirety.

FIELD OF THE INVENTION

Microbial processes and microbial compositions are disclosed that enhance crop production, increase plant defensive processes and/or decrease the level of plant pathogens.

BACKGROUND OF THE INVENTION

Microbes have previously been used in agriculture. Examples include those disclosed in U.S. Pat. Nos. 4,952,229; 6,232,270 and 5,266,096.

Chitin has also been used in agriculture either as a protein complex (U.S. Pat. No. 4,536,207) or in combination with various microbes (U.S. Pat. Nos. 6,524,998 and 6,060,429)

Chitosan in combination with other components has been used in agricultural applications. See e.g. U.S. Pat. Nos. 6,649,566; 4,812,159; 6,407,040; 5,374,627 and 5,733,851. It has also been used to treat cereal crop seeds. See U.S. Pat. No. 4,978,381. U.S. Pat. No. 6,524,998 also discloses that chitosan can be used in combination with specific microbes for agricultural use.

Notwithstanding the foregoing, there is a need to provide improved microbial compositions and processes that improve crop yield and reduce the amount of liquid fertilizer, conventional fungicides and insecticides used in agricultural and horticultural applications.

SUMMARY OF THE INVENTION

Microbial processes and microbial compositions are disclosed that enhance crop production, increase plant defensive processes and/or decrease the level of plant pathogens. The compositions comprise a microbial composition and liquid fertilizer, preferably a liquid fertilizer that contains at least soluble nitrogen. The composition can be applied immediately to soil, foliage, seeds or seedlings. Alternatively, the composition may be activated by incubation for up to about seven days to form an activated composition. The incubation conditions influence the properties of the consortium after incubation.

The soluble nitrogen in the liquid fertilizer preferably comprises an organic source of nitrogen such as urea or a nitrogen containing inorganic salt such as ammonium hydroxide, ammonium nitrate, ammonium sulfate, ammonium pyrophosphate, ammonium thiosulfate or combinations thereof. Aqua ammonia (20-24.6% anhydrous ammonia) can also be used. The type and amount of soluble nitrogen used will depend on the particular application including type of plant or crop and soil conditions. In some cases, the amount of soluble nitrogen can be decreased because the nitrogen oxidizing bacteria increase the efficiency of nitrogen use from the soluble nitrogen source.

In one embodiment, the compositions comprise one or more lactic acid producing bacteria, one or more nitrogen fixing bacteria, and liquid fertilizer comprising soluble nitrogen. In preferred embodiments, there are multiple genera and/or species of lactic acid bacteria and nitrogen fixing bacteria.

Lactic acid bacteria include *Lactobacillus paracasei* ss. *paracasei*, *Lactobacillus acidophilus*, *Lactobacillus delbrueckii* ss. *bulgaricus* and *Lactobacillus brevis*. Other *Lactobacilli* include those deposited with the American Type Culture Collection (ATCC) Manassas, Va., US and other depositories known to the skilled artisan.

Nitrogen fixing bacteria include *Rhizobium japonicum*, *Clostridium pasteurianum* and *Azotobacter vinelandii*. Other nitrogen fixing bacteria include those deposited with the ATCC and other depositories known to the skilled artisan.

In additional embodiments, the composition further comprises microorganisms that solubilize/mineralize sources of potassium, phosphorous and/or organic carbon.

In other embodiments, the composition further comprises at least one, two or all of *Bacillus subtilis* (SILoSil® BS) *Bacillus thuringiensis* strains HD-1 and HD-73 (SILoSil® BT), and *Trichoderma harzianum* (TRICHOSIL).

In the preferred embodiment the composition comprises HYTa and liquid fertilizer. HYTa is a consortium of microorganisms which includes *Lactobacteria*, nitrogen fixing bacteria, microorganisms that solubilize/mineralize sources of potassium, phosphorous and organic carbon, *Bacillus subtilis* (SILoSil® BS) *Bacillus thuringiensis* strains HD-1 and HD-73 (SILoSil® BT), and *Trichoderma harzianum* (TRICHOSIL). HYTa was deposited pursuant to the Budapest Treaty with the ATCC on May 19, 2010 with an assigned deposit designation of PTA-10973.

In still other embodiments, the composition further comprises at least one of chitin, chitosan, glucosamine and amino acids.

Any of the foregoing compositions can be applied to soil, seed, seedling or plant foliage.

However, in a preferred embodiment, the composition is incubated for one to 7 days to activate the microbes in the composition. In the presence of soluble nitrogen, nitrogen fixing bacteria are induced to reproduce. When the composition is additionally incubated with chitin, chitosan, glucosamine and/or amino acids, certain microorganisms in the composition are induced to reproduce thereby producing a composition with enhanced properties. Such properties include the ability to enhance crop production, increase plant defensive processes and/or decrease the level of plant pathogens.

The treatment of soil, seed, seedlings and foliage can also include repeated applications of the above compositions as well as treatment with one or more of HYTa, chitin, chitosan, glucosamine and amino acids.

The application of the disclosed compositions allows for the elimination or significant reduction in the amount of fertilizer, fungicide and/or insecticide used in agricultural applications. In some embodiments, the use of the microbial formulations results in a decrease in the amount of greenhouse gas emissions.

BRIEF DESCRIPTION OF THE FIGURE

FIG. 1 is a graph showing salt concentration in soil treated with HYTa plus UAN or untreated soil. The data in FIG. 1 are also presented in Table 6, below.

DETAILED DESCRIPTION

The following describes the preferred embodiments that use HYTa in combination with liquid fertilizer.

Liquid Fertilizer

As used herein, the term "liquid fertilizer" refers to an aqueous solution or suspension containing soluble nitrogen. The soluble nitrogen in the liquid fertilizer preferably comprises an organic source of nitrogen such as urea or a nitrogen containing inorganic salt such as ammonium hydroxide, ammonium nitrate, ammonium sulfate, ammonium pyrophosphate, ammonium thiosulfate or combinations thereof. Aqua ammonia (20-24.6% anhydrous ammonia) can also be used. Liquid fertilizer does not include chitin, chitosan, glucosamine, amino acids HYTb and HYTc, although such components may be added to the liquid fertilizer as disclosed herein.

HYTa

As used herein, the term "HYTa" refers to a consortium of microbes derived from fertile soil samples and commercial sources. HYTa was deposited pursuant to the Budapest Treaty with the American Tissue Type Culture (ATTC), Rockville, Md., on May 19, 2010 with an assigned deposit designation of PTA-10973.

Table 1 identifies some of the microbes in HYTa that are believed to be responsible for the beneficial effects observed when it is used in combination with liquid fertilizer to treat soil and/or foliage.

TABLE 1

| Bacteria |
|---|
| I. *Azotobacter* |
| 1. *Azotobacter vinelandii* |
| I. II. *Clostridium* |
| 1. *Clostridium pasteurianum* |
| 2. *Clostridium beijerinckii* |
| 3. *Clostridium sphenoides* |
| 4. *Clostridium bifermentans* |
| I. III. *Lactobacillus* |
| 1. *Lactobacillus paracasei* ss. *paracasei* |
| 2. *Lactobacillus acidophilus* |
| 3. *Lactobacillus delbrueckii* ss. *Bulgaricus* |
| 4. *Lactobacillus brevis* |
| I. IV. *Bacillus* |
| 1. *Bacillus amyloliquefaciens* (*Bacillus subtilis* ((SILoSil ® BS)) |
| 2. *Bacillus thuringiensis* var. *kurstakii* (*Bacillus thuringiensis* (Strains HD-1)) |
| 3. *Bacillus thuringiensis* var. *canadensis* (*Bacillus cereus* group) |
| 4. *Bacillus pasteurii* (*Bacillus cereus* group) |
| 5. *Bacillus sphaericus* (subgroup I, III, and IV) |
| 6. *Bacillus megaterium* (subgroup A) |
| I. V. *Acetobacter* |
| 1. *Acetobacter aceti* ss. *liquefaciens* |
| 2. *Acetobacter aceti* ss. *xylimum* |
| I. VI. *Enterococcus* |
| 1. *Enterococcus faecium* (subgroup A) |
| I. VII. *Pediococcus* |
| 1. *Pediococcus pentosaceus* |
| I. VII. *Rhizobium* |
| 1. *Rhizobium japonicum* |
| Fungi |
| I. *Saccharomyces* |
| 1. *Saccharomyces cerevisiae* |
| I. II. *Penicillium* |
| 1. *Penicillium roqueforti* |
| I. III. *Monascus* |
| 1. *Monascus ruber* |
| I. IV. *Aspergillus* |
| 1. *Aspergillus oryzae* |
| I. V. *Trichoderma* |
| 1. *Trichoderma harzianum* (TRICHOSIL) |
| Plantae |
| I. *Arthrospiro* |
| 1. *Arthrospira platensis* |
| I. II. *Ascophyllum* (Algae) |
| 1. *Ascophyllum nodosum* |

Other microorganisms contained in HYTa: *Nitrobacter, Nitrosomonads, Nitrococcus, Pseudomonas, Micrococcus luteus, Actinomycete, Azotobacter vinelandii, Lactobacillus casei, Trichoderma harzianum, Bacillus licheniformis, Pseudomonas fluorescens* and *Streptomyces.*

Active microbes in HYTa include nitrogen-fixing microorganisms native to soil. These are *Azotobacter vinelandii* and *Clostridium pasteurianum. Bacillus subtilis* provides enzymes for breaking down plant residue. *Bacillus cereus* provides additional enzymes to break down plant residue and penicillinase to decease unwanted bacteria. *Bacillus megaterium* degrades complex sugars after crop residue breakdown. *Lactobacillus* provides food for the microbes in HYTa and controls the pH of the environment. The *Nitrosomonas* organisms oxidize ammonia to nitrite ($NO_2$) while the *Nitrobacter* microbes oxidize nitrite to nitrate ($NO_3$).

An important property of HYTa is the fixation of atmospheric nitrogen. The nitrogen fixing capability of the microbes in HYTa is enhanced by the assistance of other organisms in HYTa. Nitrogen fixation requires that phosphorous (P), potassium (K) and organic carbon (C) be available. HYTa contains microbes that are able to solubilize/mineralize P, K, and C within the soil. In addition, the nitrogen fixing bacteria provide a source of nitrogen for the other microbes in HYTa.

Nitrogen fixation may occur in a non-symbiotic manner by the bacteria *Azotobacter vinelandii*, and *Clostridium pasteurianum* present in HYTa or in a symbiotic manner as occurs in root nodules by way of the *Rhizobium* bacteria, e.g., *Rhizobium japonicum.*

The carbon required by the nitrogen fixing microbes in HYTa is provided by the C decomposers which solubilize/mineralize the complex organic compounds in soil into simple compounds such as sugars, alcohols, and organic acids. The C decomposers include many of the above identified microbes.

Phosphorus is necessary for the nitrogen fixing microbes to proliferate and is obtained from the metabolic activity of the P decomposers which solubilize/mineralize immobilized phosphorus in the soil into a bio-available phosphorus nutrient. P decomposers in HYTa include *Acetobacter, Bacillus subtilis, Pseudomonas fluorescens* and *Micrococcus luteus.*

Potassium is necessary for the nitrogen fixing microbes to proliferate and is obtained from the metabolic activity of the K decomposers which convert immobilized phosphorus in the soil into a bio-available potassium nutrient. K decomposers in HYTa include *Pseudomonas fluorescens.*

Three important microbes in HYTa are *Bacillus subtilis* (SILoSil® BS) *Bacillus thuringiensis* strains HD-1 and HD-73 (SILoSil® BT), and *Trichoderma harzianum* (TRICHOSIL). These organisms are present ATTC deposit PTA-10973. They were originally obtained from Biotecnologia Agroindustrial S.A. DE C.V., Morelia, Michoacan, Mexico.

*Bacillus subtilis* (SILoSil® BS) is a Gram positive bacterium which is mesophilic and grows at an optimum temperature between 25 and 35° C. It is aerobic and can grow in anaerobic conditions and utilizes a wide variety of carbon sources. It contains two nitrate reductases, one of which is utilized for nitrogen assimilation. It is capable of secreting amylase, proteases, pullulanases, chitinases, xylanases and lipases.

*Bacillus thuringiensis* (Strains HD-1 and HD-73 (SILoSil® BT)) are Gram Positive anaerobic facultative bacteria, in the form of peritrichous flagella. Strains HD-1 and HD-73 synthetizes crystals with diverse geometric forms of protein and insecticide activity during the spore period. Strains HD-1 and HD-73 secret exochitinase when in a chitin containing medium and can be utilized for the degradation of the crustacean residues during the production of chitooligosaccharides.

*Trichoderma harzianum* (TRICHOSIL) is a saprophyte fungus. It exhibits antibiotic action and biological competition and for this reason has biological control properties. It produces enzymes that degrade cell walls or a combination of such activities. It produces glucanases, chitinases, lipases, and extracellular proteases when it interacts with some pathogenic fungi, such as *Fusarium*.

As shown above the metabolism of each group of bacteria are closely interdependent and live in a close symbiotic association for the proper performance of HYTa.

Besides carbon, hydrogen, phosphorus, potassium, sulfur and various trace elements, a mix of special growth factors, such as vitamin B complex, free L-amino acids, and ultra-soluble trace elements are important for optimal bacterial growth. Fermenting yeasts are incorporated into HYTa to provide these components. The $N_2$ fixing process requires large amounts of ATP. The amount of ATP naturally present is not enough to fuel biological $N_2$ fixation. The fermentation of the yeast in HYTa compensates for the large energy deficit. The ATP is used in the biological nitrogen fixation process.

HYTa contains enzymes and beneficial soil microorganisms that replace those that have been depleted due to the excessive use of chemicals which results in diminishing crop yields. By increasing the microbial activity in the soil with HYTa, the bacteria causes the nutrients and micro-elements to be absorbed (mineralized) more efficiently and effectively by plants.

Humus is transformed by the microorganisms in HYTa that protect both soil structure and the capability of the cells to resist free radicals. This increases the nutrients and the essential elements available in the soil that can be absorbed by plants.

The use of HYTa in liquid fertilizer alone or in combination with chitin, chitosan, glucosamine and/or amino acids (1) provides nutrients and elements in the soil that increase crop yields by 25-55%, (2) reduces greenhouse gas emissions, (3) increases the efficiency of mineral fertilizers (4) reduces the use of conventional fungicides and other pesticides, (5) increases the production of plant growth regulators, (6) improves soil structure, tilth, and water penetration and retention, (7) cleans up chemical residues and (8) shifts soil pH toward neutral pH.

Compositions

HYTa in liquid fertilizer can be used, alone or in combination, with one or more components selected from the group of one or more amino acids, chitin, chitosan and/or glucosamine. In some cases, Acetyl-D-glucosamine can be included in the composition. The composition includes any and all combinations of the aforementioned components. Particularly preferred combinations include: (1) HYTa, liquid fertilizer and chitin; (2) HYTa, liquid fertilizer and chitosan; (3) HYTa, liquid fertilizer and glucosamine; (4) HYTa, liquid fertilizer and amino acids; (5) HYTa, liquid fertilizer, chitin and amino acids; (6) HYTa, liquid fertilizer, chitin, chitosan and amino acids; (7) HYTa, liquid fertilizer, chitosan, glucosamine and amino acids; (8) HYTa, liquid fertilizer, chitosan and glucosamine; (9) HYTa, liquid fertilizer, chitin, chitosan, glucosamine and amino acids, (10) HYTa, liquid fertilizer and humic/fulvic acids and/or humates.

When HYTa is grown in the presence of liquid fertilizer, chitin, chitosan and/or amino acids it may contain residual chitin, chitosan and/or amino acids. Under such circumstances, the composition and can be applied directly to soil, seed, seedlings or plant foliage. Alternatively, one or more of amino acids, chitin, chitosan and/or glucosamine can be added to supplement the components already in the composition or to change its composition.

As used herein, the term "amino acids" refers to a composition containing two or more amino acids. Amino acids include tryptophan, histidine, threonine, tyrosine, valine, methionine, isoleucine, leucine, phenylalanine, lysine, aspartic acid, cysteine, glutamic acid, glutamine, serine, glycine, alanine, proline, asparagine and arginine. In preferred embodiments, amino acids are provided by use of HYTb (See below).

As used herein, the term "chitin" refers to a biopolymer consisting predominantly of repeating units of beta-1-4-linked N-acetyl-D-glucosamine. Chitin is found in the natural environment as a primary structural material of the exoskeleton of animals such as Arthropoda, e.g., crustaceans, insects, spiders, etc., Mollusca, e.g., snails, squid, etc., Coelentara, e.g., organisms such as hydoids and jellyfish, and Nematoda, such as unsegmented worms. Chitin is also found in various fungi including members of the genus *Fusarium*. Chitin can be extracted from these natural sources by treatment with alkali, or by a biodegradation process. The molecular weight of chitin varies depending on its source and method of isolation. In preferred embodiments, the chitin is derived as a solid from the biodegradation of chitin containing Arthropods as described in the Bioderpac applications. It is preferred that the chitin have a diameter of about 50 to 75 microns to facilitate its application via drip and spray irrigation systems.

As used herein, the term "chitosan" is a polysaccharide consisting predominantly of repeating units of D-glucosamine. Chitosan is obtained by deacetylation of chitin. The degree of deacetylation as compared to chitin is preferably greater than 50%, 60%, 70%, 80%, 85%, 90% and 95%. It is preferred that the level of deacetylation be sufficient to render the chitosan water soluble at acidic pH. The molecular weight of chitosan varies depending on its source and method of isolation. Chitosan includes chitosan oligomers. In preferred embodiments, chitosan is precipitated at pH 9.0 from the aqueous fraction obtained from the biodegradation of chitin containing Arthropods such as described in the Bioderpac applications.

As used herein, the term "chitosan oligomer" refers to chitosan having 2 or more repeating units of D-glucosamine and, in the case of incomplete deacetylation of chitin, one or more units of N-acetyl-D-glucosamine. In preferred embodiments, the chitosan oligomers are derived from the aqueous fraction generated in the biodegradation of chitin containing Arthropods such as described in the Bioderpac applications. In some embodiments chitosan oligomers are used as the second component of the microbial composition.

As used herein, the term "glucosamine" refers to an amino monosaccharide. In preferred embodiments it is the sugar residue that forms the backbone of the biopolymers chitin and chitosan. Glucosamine is present in the aqueous fraction generated during the biodegradation of chitin containing Arthropods such as described in the Bioderpac applications. Glucosamine induces plants to make chitinase as a defense to chitin containing pathogens.

HYTb and HYTc

As used herein, the term "HYTb" refers to the aqueous fraction and "HYTc" refers to the solid fraction obtained from the biodegradation chitin containing organisms. The biodegradation of Arthropods such as shrimp waste to make HYTb and HYTc is disclosed in US Patent Application Publication 2011/0151508. The biodegradation of chitin containing organisms such as filamentous fungi, yeast and insects to form HYTb and HYTc is described in US Patent Application Publication 2012/0329135 each of which are incorporated herein by reference.

By way of example, in the arthropod biodegradation process a microbial composition is used to degrade the arthropod or waste components of the arthropod. It is a lactic acid fermentation process. The microbial composition contains microbes that produce enzymes that can degrade the chitin containing components of the arthropod to chitin, chitosan, N-acetyl glucosamine and glucosamine. It also contains microbes that produce enzymes that can degrade proteins and fats to produce amino acids and lipids. A preferred microbial composition for arthropod degradation is referred to as HQE. HQE was deposited pursuant to the Budapest Treaty with the American Type Culture Collection (ATCC) Manassas, Va., USA on Apr. 27, 2010 and given Patent Deposit Designation PTA-10861.

In a preferred embodiment, the marine arthropod is a crustacean and the preferred crustacean is shrimp. Shrimp by-product comprises shrimp cephalothorax and/or exoskeleton.

In the biodegradation process, it is preferred that the fermentation be facultative aerobic fermentation. It is also preferred that the fermentation is carried out at a temperature of about 30° C. to 40° C. The pH is preferably less than about 6, more preferably less than about 5.5. However, the pH should be maintained above about 4.3. The fermentation is carried out for about 24-96 hours. In some embodiments, the fermentation is carried out for about 24-48 hours and more preferably 24-36 hours. These fermentation times are far shorter than the typical prior art fermentation times of 10 to 15 days to achieve substantially the same amount of digestion, albeit without detectable formation of chitosan and glucosamine.

The separation of the mixture is preferably by centrifugation. (e.g. about 920 g). Gravity separation can also be used but is not preferred because of the time required to achieve separation.

The mixture separates in to three fractions: solid, aqueous and lipid. The solid fraction comprises chitin and is designated HYTc. The aqueous fraction comprises protein hydroysate, amino acids, chitosan and glucosamine and is designated HYTb. The lipid fraction comprises sterols, vitamin A and E and carotenoid pigments such as astaxanthine.

It is preferred that HQE be used in the biodegradation process. In other embodiments, it is preferred that previously prepared HYTb be added to HQE or the fermentation broth. As described above, HYTb contains amino acids, chitosan, glucosamine and trace elements including calcium, magnesium, zinc, copper, iron and manganese. HYTb also contains enzymes such as lactic enzymes, proteases, lipases, chitinases, lactic acid, polypeptides and other carbohydrates. HYTb can also contain dormant microorganisms from a prior biodegradation process. Such microorganisms can become reactivated and, in combination with HQE, contribute to a more robust biodegradation process as compared to when HQE is used by itself as otherwise described herein More particularly, the process includes the following steps:

a. Activation of the microbial cells in a sugar base solution to enhance its growth and the biomass formation.

b. Milling of the shrimp by-products (cephalothorax and exosqueleton) to make a homogeneous paste.

c. Homogeneous mixing of the shrimp by-product paste with at least 10% of the activated inoculum.

d. Adjustment of the pH values to less than 6.0 in the mixture using a citric acid solution to inhibit the growth of microorganisms and to promote the development of microbial cells that constitute the inoculum.

e. Fermentation of the mixture in a non-continuous agitated system at temperatures within a range of 30 to 40° C. at least for at least 96 hours maintaining pH at less than 5.0. The pH is monitored periodically. If the pH rises above 5.0, a citric acid buffer is added in an amount to maintain the pH below 5.0.

f. Centrifugation of the ferment to separate the three principal fractions: chitin, liquid hydrolysate and pigmented paste.

g. Rinsing of the crude chitin and recollection of the rinse water to recuperate fine solids or minerals.

h. Drying of the chitin and storage.

i. Drying and storage of the liquid hydrolysate.

j. The pigmented paste (lipid fraction) is stored in closed recipients for conservation.

The process and operational fundamentals are better understood with reference to the following detailed description.

Activation of Microbes

The inoculum of HQE has a concentration of microbes of about 2.5 to 3.0% (w/v). HQE is activated by dilution to 5% in sugar cane solution (3.75% final concentration of sugar cane), and incubated at 37° C. for 5 days. HYTb (10 ml per liter of culture) is preferably added to provide a source of minerals and naturally derived amino acids. The cellular growth of the microorganisms was estimated by optical density measured at 540 nm. The activation is complete at an optical density of about 1.7. The concentration of microbes after activation is about 1.9 to 3.0% (w/v).

Preparation of Samples

The shrimp by-products samples are obtained from shrimp processing plants. Slightly thawed and minced residue (1500 g by batch) is mixed with 99 grams of sugar cane (final concentration 6.6% wt %) and 85.5 ml of activated HQE 5% (v/w) (optical density of cell=1.7). Then the pH is adjusted to 5.5 using 2 M citric acid.

Fermentation Control

The mixture is incubated at 36° C. with a non-continuous agitation for 96 h. During the fermentation process, the pH is monitored by using a potentiometer, and the total titratable acidity (TTA, %) was determined by titration with 0.1 N NaOH until a pH of 8.5 is obtained. The TTA is expressed as a percentage of lactic acid.

Conditions of Separation

The fermentation product is a viscous silage which has an intense orange color, due to the astaxanthine presence. The ensilage is centrifuged (5° C.) at 1250 rpm (930 g) for 15 min to obtain the chitin, the liquid hydrolysates, and the pigment paste. The upper phase (pigment paste) is separated manually. The liquid hydrolysates are separated by decantation, and the sediment that constitutes the raw chitin is washed with distilled water to separate fine solids. The resulting liquid is collected and dried. The raw chitin, liquid hydrolysates and fine solids are dried at 60° C. All the fractions are stored to protect them from light.

Other microbial compositions for the production of HYTb and HYTc are set forth in the following Table 2.

TABLE 2

Culture Composition

| Microorganism | 1 | 2 | 3 | 4 | 5 | 6 | 7 | 8 | 9 | 10 |
|---|---|---|---|---|---|---|---|---|---|---|
| Bacillus subtilis | X | X | X | X |  | X | X | X |  | X |
| Bacillus cereus | X | X |  | X |  | X |  | X |  | X |
| Bacillus megaterium | X | X |  |  |  |  |  |  |  |  |
| Azotobacter vinelandii | X | X |  | X |  | X |  | X |  | X |
| Lactobacillus acidophilus | X | X | X | X | X |  | X | X | X |  |
| Lactobacillus casei | X | X |  | X | X |  |  | X | X |  |
| Trichoderma harzianum | X | X | X | X |  | X | X | X |  | X |
| Rhizobium japonicum | X | X |  | X |  | X |  | X |  | X |
| Clostridium pasteurianum | X | X |  |  | X | X |  |  | X | X |
| Bacillus licheniformis | X | X | X |  | X | X | X |  |  | X |
| Pseudomonas fluorescens | X | X | X |  | X | X |  |  |  |  |
| Bacillus thuringiensis | X |  |  |  |  |  | X | X | X | X |
| Streptomyces | X |  |  |  | X | X | X | X | X | X |
| Nitrobacter | X |  |  |  |  |  | X | X | X | X |
| Micrococcus | X |  |  |  |  |  | X | X | X | X |
| Proteus vulgaris | X |  |  |  |  |  | X | X | X | X |

These microorganisms are preferably derived from HQE and are referred to as *Bacillus subtilis* ((SILoSil® BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73 (SILoSil® BT), *Streptomyces* (Bioderpac, 2008), *Micrococcus* (Bioderpac, 2008), *Nitrobacter* (Bioderpac, 2008) and *Proteus* (Bioderpac, 2008). Each of these organisms can be readily isolated from HQE and recombined to form the disclosed microbial composition to degrade arthropods to make HYTb and HYTc.

HYTb contains amino acids (about 12 wt %), chitosan (about 1.2 wt %), glucosamine (about 1 wt %) and trace elements (about 6 wt %) including calcium, magnesium, zinc, copper, iron and manganese. It also contains enzymes such as lactic enzymes, proteases, lipases, chitinases among others, lactic acid, polypeptides and other carbohydrates. The specific gravity of HYTb is typically about 1.050-1.054. The average amino acid content in HYTb for certain amino acids is set forth in Table 2.

TABLE 3

Amino acid profile dry powder hydrolysates (mg per g dry weight)

| Amino acid | Dry powder hydrolysates |
|---|---|
| Aspartic acid | 38 |
| Glutamic acid | 39 |
| Serine | 16 |
| Histidine | 9 |
| Glycine | 28 |
| Threonine | 14 |
| Alanine | 36.1 |
| Proline | 25.8 |
| Tyrosine | 70 |
| Arginine | 22.2 |
| Valine | 20 |
| Methionine | 16.4 |
| Isoleucine | 18.3 |
| Tryptophan | 3.1 |
| Leucine | 23 |
| Phenylalanine | 39 |
| Lysine | 13 |
| Total | 431 |

In some embodiments, HYTb is either combined with HYTa or used separately as a soil amendment and/or as a foliage spray.

The primary component of HYTc is chitin. It has an average molecular weight of about 2300 daltons and constitutes about 64 wt % of the composition. About 6% of HYTc contains minerals including calcium, magnesium, zinc, copper, iron and manganese, about 24 wt % protein and 6% water. It has a specific gravity of about 272 Kg/m$^3$. In some embodiments, HYTc can constitute a second component that is either combined with HYTa or used separately as a soil amendment and/or as a foliage spray.

The microbes in HYTa require the trace elements calcium, magnesium, sulfur, boron, manganese, zinc, molybdenum, iron, copper, sodium, and silicon. These important trace elements can be often obtained from toxic chemical reactions which are not suitable for organic certified products. Accordingly, it is preferred that these trace elements be obtained from an organic source such as HYTb and/or HYTc.

Activation of HYTa

In preferred embodiments, HYTa is activated by incubating an inoculum of HYTa in an aqueous solution containing soluble nitrogen (liquid fertilizer) for 24-168 hours to allow the microbes to grow and reproduce before being used in the process of treating soil, seeds, seedlings and/or plant foliage. The conditions of the incubation influence the overall initial properties of composition.

In one embodiment, an inoculum of HYTa is diluted with water containing soluble nitrogen in a ratio of 1/100 and allowed to incubate at a temperature of approximately 36° C. at a pH of 6.8-7.1 for about 24 to about 168 hours (7 days). HYTb can optionally be used during this activation. The nitrogen fixing microbes *Azotobacter vinelandii* and *Clostridium pasteurianum* proliferate under reduced nitrogen growth conditions. In addition, as the oxygen concentration decreases, *Lactobacilli*, including *Lactobacillus acidophilus* and *Lactobacillus casei*, proliferate.

The HYTa containing composition obtained after this incubation retains the beneficial properties of HYTa but is particularly suited as a soil amendment for treatment of nitrogen-depleted soils given the nitrogen-fixation capabilities of *Azotobacter vinelandii* and *Clostridium pasteurianum*.

If soil pathogens such as filamentous fungi from the genus *Fusarium* or nematodes are present, or believed to be present, HYTa containing composition can be activated under substantially the same conditions but in the presence of chitin. The chitin stimulates the expansion of the chitin responsive microbes such as *Pseudomonas fluorescens, Trichoderma harzianum, Bacillus thuringiensis, Streptomyces* sp., *Micrococcus* sp., and *Bacillus subtilis*. HYTa obtained under these conditions has an antifungal, fungicidal, antinematode, nematodicidal and insecticidal properties to the extent such pathogens contain chitin. Such microbial compositions can be applied directly to the soil or to seed, seedlings and/or plant foliage. Such microbial compositions also have the ability to fix nitrogen as in the aforementioned incubation in the absence of chitin.

In addition to incubating with chitin, the composition can be activated with chitin and amino acids. A preferred source of chitin is HYTc. When HYTc is used the protein and minerals in HYTc are also present during the activation.

Further, the HYTa containing composition can be activated in the presence of amino acids and chitosan. A preferred source of amino acids and chitosan is HYTb or HYTd (see below). When HYTb and/or HYTd is used glucosamine and the other components of HYTb or HYTd are also present during the activation.

Optionally, HYTa can be incubated with chitin, amino acids and chitosan. A preferred source of chitin is HYTc. A preferred source for amino acids and chitosan is HYTb and/or HYTd. When HYTb and/or HYTd and HYTc are used the other components in these formulations are also present during activation.

HYTd

HYTd is similar to HYTb but has higher concentrations of glucosamine and chitosan. The preparation of HYTd is disclosed in US Patent Application Publication 2012/0329650 which is incorporated herein by reference.

HYTd is obtained by fermenting chitin with a microbial composition such as HQE suspended in HYTb. The process is similar to that described above for the production of HYTb and HYTc except that the substrate is chitin, e.g. HYTc, rather than chitin containing Arthropods. HYTd is the liquid fraction obtained from this fermentation.

HYTb already contains chitosan (about 0.5-1.5 wt %) and glucosamine (about 0.5-1.5 wt %). The amount of chitosan and glucosamine in HYTd ranges from about 2 wt % to 2.5 wt % chitosan and from about 2 wt % to 5 wt % glucosamine. This represents an increase in the amount of chitosan and glucosamine as compared to HYTb of about 0.5 wt % to 2.5 wt % chitosan and from about 0.5 wt % to 5 wt % glucosamine.

HYTd when undiluted is similar to HYTb but contains higher amounts of chitosan and glucosamine. HYTd contains amino acids (about 5 to 12 wt %) and trace elements (about 6 wt %) including calcium, magnesium, zinc, copper, iron and manganese. It also contains enzymes (such as lactic enzymes, proteases, lipases, chitinases among others), lactic acid, polypeptides and other carbohydrates. In some embodiments, the degree of acetylation of the produced chitosan is 20% or less, preferably 15% or less, more preferably 10% or less, still more preferably preferable 8% or less and most preferably 5% or less. The average amino acid content in HYTd for certain amino acids is similar to HYTb.

HYTd preferably comprises 12 wt % L-amino acids (Aspartic acid, Glutamic acid Serine, Histidine, Glycine, Threonine, Alanine, Proline, Arginine, Valine, Methionine, Isoleucine, Tryptophan, Phenylalanine, Lysine and threonine) and 5 wt % glucosamine and chitosan. HYTd also preferable contains one or more or all of soluble minerals (P, Ca, Mg, Zn, Fe and Cu), enzymes and lactic acid from the chitin digestion process as well as other polysaccharides.

Use of Activated HYTa Containing Compositions

Activated HYTa containing compositions can be used alone or in combination with other components such as chitin, chitosan, glucosamine and amino acids to treat soil, seed, seedlings or foliage. In some embodiments, combinations of these components can be applied as a mixture. In other embodiments, they can be applied separately. In still other embodiments, the components can be applied at different times.

In one embodiment, activated HYTa can be applied to soil, seeds or seedlings, or used in foliar applications by direct application to foliage. However, when plant pathogens are present, it is preferred that microbial composition comprises activated HYTa, chitin and/or chitosan. Alternatively, the HYTa can be activated in the presence of chitin. Chitosan is known to have bactericidal and fungicidal properties, as well as its ability to stimulate plant growth and to induce plant resistance to pathogens. In other embodiments, glucosamine is a part of the microbial composition In a preferred embodiment, the activated HYTa/liquid fertilizer containing composition, alone or in combination with chitin (preferably HYTc) and/or chitin, chitosan, and amino acids (preferably HYTb and/or HYTd and HYTc), is applied to soil, seeds, seedlings and/or foliage. It is preferred that HYTa/liquid fertilizer be used in combination with chitin, chitosan, glucosamine and amino acids. HYTc is the preferred source of chitin while HYTb and/or HYTd is the preferred source of chitosan, glucosamine and amino acids. However, the components of the microbial composition namely HYTa, chitin, chitosan, glucosamine and amino acids can be applied separately or in any combination or sub-combination. They can be applied at the same time or sequentially, in any given order. However, the preferred mode of application is to initially apply all at the same time. The application of the foregoing components provide for the direct treatment of plant pathogens, the induction of plant pathogen resistance pathways, and the nourishment of the HYTa microbes, the indigenous nonpathogenic soil flora, and the plant.

When soil is initially treated with a microbial composition comprising activated HYTa in liquid fertilizer alone, the microbes present in the composition have an opportunity to populate the soil and to alter its taxonomic composition. In some situations, the initial colonization by HYTa provides little or no nutrients to the plant. In such instances, it is important to maintain a nutrient reserve to sustain both the growth of the microbes while colonizing the rizosphere and the growth of the plants in the soil. It may be necessary to repeat the application of HYTa, depending on the plant's growth cycle and nutritional regime. In other cases, it may be sufficient to provide additional applications of amino acids, chitin and/or chitosan, e.g. HYTb and HYTc, to the previously treated soil.

When HYTa is used in combination with, for example, HYTb and/or HYTd and HYTc, addition nutrients are available to the HYTa microbes and the plants present in the treated soil.

Table 4 sets forth a typical fourteen week program for the application of HYTa in liquid fertilizer, HYTb and HYTc to drip irrigated crops cultivated in soil. The values are per hectare. For HYTa and HYTb, the values represent liters per week. For HYTc, the values represent kilograms per week.

TABLE 4

| Lts/kg/Week | W 1 | W 2 | W 3 | W 4 | W 5 | W 6 | W 7 | W 8 | W 9 | W 10 | W 11 | W 12 | W 13 | W 14 |
|---|---|---|---|---|---|---|---|---|---|---|---|---|---|---|
| HYT-A | 3 | 0 | 0 | 1 | 0 | 1 | 0 | 1 | 0 | 1 | 0 | 1 | 0 | 1 |
| HYT-B | 10 | 5 | 0 | 3 | 2 | 3 | 2 | 3 | 2 | 3 | 2 | 3 | 2 | 3 |
| HYT-C | 1 | | | 1 | | | | 1 | | | | 1 | | |

Uses with Liquid Nitrogen Fertilizers can be with pop-up fertilizers (in furrow), starters fertilizers (2×2 placement) and side-dress applications (dribble or knife—in applications usually 22-30 days after planting).

The pulse in which the HYTa/liquid nitrogen containing composition is injected to the irrigation system should be one in which the composition is able to reach the root system and stay there over night while the system is off. For maximum performance of HYTc, it should be applied at the same time as a mixture with HYTa. The protocol should be continued as long as the plant continues in production. This protocol covers all plant stages including germination, root formation, plant growth, flowering, fruit setting, fruit formation harvesting and re-harvest. This protocol is designed for maximum yield potential covering nutritional aspects, biostimulation aspects and protection against diseases such as nematodes and fungi.

The process can be carried out by contacting soil to form a treated soil. In some cases the process is repeated. In some cases, plants, seedlings or seeds are already present in the soil prior to treatment with the microbial composition. In other cases, plants, seedlings or seeds are transplanted to the soil after treatment with the composition.

In general, before application the number of hectares or acres to be treated is determined. Then the recommended amount of activated HYTa containing composition per hectare or acre is multiplied by the area to be treated and diluted in sufficient water to irrigate or spray the soil or crop on the area to be treated. The same procedure can be followed for liquid HYTb and/or HYTd. HYTc, being a solid, can be applied directly as a solid or as a suspension in water. HYTc is preferably ground to micron size particles prior to use.

The process can be carried out with infertile soil. Such soils generally are those were at least one of low cation exchange capacity, low water holding capacity, low organic matter content and low levels of available nutrients is present. In general, infertile soil does not support vigorous plant growth and/or produces low crop yields.

For non-soil systems such as hydroponics, the same protocol applies but with a daily distribution following the ferti-irrigation program.

The compositions can be used in connection with any plant including but not limited to alfalfa, banana, barley, broccoli, carrots, corn, cotton, cucumber, garlic, grapes, leek, melon, onion, potato, raspberry, rice, soybean, squash, strawberry, sugarcane, tomato and watermelon.

Although the disclosure is directed primarily to the use of the disclosed microbial compositions for agricultural applications, such compositions or their components and processes can also be used in horticultural applications to improve the production of foliage and flowers and decrease the use of conventional insecticides and fungicides.

When activated HYTa in liquid fertilizer (alone or in combination with one or more of chitin, chitosan, glucosamine, amino acids, HYTb and/or HYTd and/or HYTc) is applied to soil, seed seedling or foliage it forms treated soil, treated seed, treated seedling, treated foliage and treated plants. Activated HYTa in liquid fertilizer is a novel microbial composition. Therefore the soil, seed, seedling, foliage and plants treated with this composition are also novel because the relative amounts of the organisms in HYTa after incubation are different than those produced by activation if HYTa in the absence of liquid fertilizer as disclosed in WO/2011/157747.

Treated soil is defined as soil that contains liquid fertilizer and one or more microbes that are unique to HYTa and dispersed within the treated soil. Such HYTa microbes can have a unique phenotype(s) and/or genotype(s) as compared to the microbes present in the soil prior to treatment with HYTa and liquid fertilizer. Microbes in HYTa that are particularly useful for detecting the presence of HYTa include *Bacillus subtilis* (SILoSil® BS), *Bacillus thuringiensis* strain HD-1, *Bacillus thuringiensis* strain HD-73 (SILoSil® BT) and *Trichoderma harzianum* (TRICHOSIL). Identification of one or more of these microorganisms can be further combined with the identification of other microbes in HYTa, if necessary, to confirm the presence of HYTa or that HYTa was present. Such other microorganisms include *Azotobacter vinelandii*, *Clostridium pasteurianum* and *Bacillus subtilis* which are present in the HYTa ATCC deposit. Each of *Bacillus subtilis* (SILoSil® BS), *Bacillus thuringiensis* strains HD-1 and HD-73 (SILoSil® BT) and *Trichoderma harzianum* (TRICHOSIL) were deposited pursuant to the Budapest Treaty with the ATCC on Oct. 7, 2011, May 31, 2012, and Oct. 6, 2011 and given Patent Deposit Designations PTA-12153, PTA-12967, and PTA-12152 respectively Treated seed, seedlings, foliage and plants are similarly defined. In these cases, the microbes of HYTa are found on the surfaces of the treated seed, seedlings, foliage and plants.

As used herein, the term "consisting essentially of" in connection with HYTa, HYTb, HYTd and HYTc means any of HYTa, HYTb, HYTd and/or HYTc alone or in combination without additional microbes.

Example 1

Corn Trials

UAN 32-0-0 is often used as a side dress application on corn at the 5-7 leaf stage to insure proper amount of nitrogen is available for optimum production. The average application of UAN is 140-160 units of N per acre.

HYTa was mixed with UAN 31-0-0 or UAN 28-0-0. The amount of HYTa and fertilerzer used per acre was about 32 oz of HYTa and about 40-45 gallons of UAN 32-0-0 or UAN 28-0-0. After 2 to 12 hours, the composition was applied as a side dress. A total of five hundred fifty acres of corn at 10 different locations were treated. The increase in the yield (bushels/acre) is set forth in Table 5.

TABLE 5

| Location | Actual Bu/Acre Increase over Control |
|---|---|
| 1 | 0.0 |
| 2 | 9.0 (*), (^) |
| 3 | 8.1 |
| 4 | 2.0 |
| 5 | 0.0 (&) |
| 6 | 0.5 |
| 7 | 23.0 |
| 8 | 2.0 |
| 9 | 37.0 |
| 10 | 8.7 |
| Total | 90.3 |
| Average of Actual Results | 9.0 |

Notes:
All of the results are based on harvester equipment yield indicators unless otherwise noted
(*) Actual results based on weigh wagon
(^) 140 units of N used rather than standard 160-180
(&) yield indicator on this equipment was calibrated in 5 bu not 1 bu so actual bu increase could be anywhere from 0-4.9; tallied as 0.

Corn treated with HYTa and UAN 32-0-0 or UAN 28-0-0 yielded an average increase of about of about 9 bushels of corn per acre as compared to plots treated with UAN 32-0-0 or UAN 28-0-0 alone.

Table 6 and FIG. 1 set forth a measurement of salt concentration in treated and untreated soil

TABLE 6

EC Results

| Location | Treated | Control | HYT A Alone | Soil Temp |
|---|---|---|---|---|
| A | 0.18 | 0.2925 | | 85 |
| B | 0.06 | 0.075 | | 86 |
| C | 0.23 | 0.208 | | 87 |
| D | 0.03 | 0.04 | | 87 |
| E | 0.18 | 0.308 | | 88 |
| F | 0.07 | 0.1175 | 0.10 | 88 |
| G | | 0.2575 | | |

*When reading data the lower the number is the lower the salt content. Low numbers are good, higher number are worse Example 2

Cotton Trials

Cotton growers often use an N-P-K mix as a side dress application on cotton between First Square and first bloom stage to insure the proper amount of nitrogen is available for optimum production. Average application is 60-90 units of N per acre.

HYTa was combined with 18-0-0-3S (derived from ammonium nitrate and ATS). A total of 180 acres were treated with an average plot size of 20 acres. One quart of HYTa was combined with about 40-45 gallons of 18-0-0-3S for each acre treated.

Estimated yields were determined by hand harvesting four, ten row feet in the control and treated plots. The following tables demonstrate the increase in lint and bales of cotton at different locations.

Location 1 Cotton Trial

TABLE 7A

| | CONTROL | | | TREATED | | |
|---|---|---|---|---|---|---|
| | WEIGHT GRAMS | BOLE COUNT | AVG BOLE WT GRAMS | WEIGHT GRAMS | BOLE COUNT | AVG BOLE WT GRAMS |
| | 887 | 135 | 6.57 | 1041 | 148 | 7.03 |
| | 767 | 128 | 5.99 | 1183 | 198 | 5.97 |
| | 1031 | 165 | 6.25 | 1004 | 161 | 6.24 |
| | 1037 | 182 | 5.70 | 1402 | 254 | 5.52 |
| AVG | 931 | 153 | 6.13 | 1158 | 190 | 6.19 |

TABLE 7B

| | CONTROL | TREATED | Difference |
|---|---|---|---|
| Lbs lint/ac | 1046 | 1319 | 273 |
| Bales/ac | 2.2 | 2.7 | 21% |

Location 2 Cotton Trial

TABLE 8A

| | Control | | | TREATED | | |
|---|---|---|---|---|---|---|
| | WEIGHT GRAMS | BOLE COUNT | AVG BOLE WT GRAMS | WEIGHT GRAMS | BOLE COUNT | AVG BOLE WT GRAMS |
| | 695 | 142 | 4.89 | 1089 | 217 | 5.02 |
| | 633 | 143 | 4.43 | 935 | 229 | 4.08 |
| | 961 | 197 | 4.48 | 1164 | 228 | 5.11 |
| AVG | 763 | 161 | 4.73 | 1063 | 225 | 4.74 |

TABLE 8B

| | CONTROL | TREATED | Difference |
|---|---|---|---|
| Lbs lint/ac | 8516 | 1191 | 340 |
| Bales/ac | 1.8 | 2.5 | 29% |

Location 3 Cotton Trial

TABLE 9A

| CONTROL | | | TREATED | | |
|---|---|---|---|---|---|
| WEIGHT GRAMS | BOLE COUNT | AVG BOLE WT GRAMS | WEIGHT GRAMS | BOLE COUNT | AVG BOLE WT GRAMS |
| 1314 | 253 | 5.19 | 1702 | 258 | 6.60 |
| 1241 | 225 | 5.52 | 1539 | 277 | 5.56 |

TABLE 9A-continued

| | CONTROL | | | TREATED | | |
|---|---|---|---|---|---|---|
| | WEIGHT GRAMS | BOLE COUNT | AVG BOLE WT GRAMS | WEIGHT GRAMS | BOLE COUNT | AVG BOLE WT GRAMS |
| | 1200 | 229 | 5.24 | 1288 | 247 | 5.21 |
| | 1202 | 233 | 5.16 | 1352 | 226 | 5.98 |
| AVG | 1239 | 235 | 5.28 | 1470 | 252 | 5.84 |

TABLE 9B

| | CONTROL | TREATED | Difference |
|---|---|---|---|
| Lbs lint/ac | 1388 | 1647 | 259 |
| Bales/ac | 2.9 | 3.4 | 16% |

Location 4 Cotton Trial

TABLE 10A

| | CONTROL | | | TREATED | | |
|---|---|---|---|---|---|---|
| | WEIGHT GRAMS | BOLE COUNT | AVG BOLE WT GRAMS | WEIGHT GRAMS | BOLE COUNT | AVG BOLE WT GRAMS |
| | 838 | 191 | 4.39 | 914 | 215 | 4.25 |
| | 893 | 201 | 4.44 | 950 | 218 | 4.36 |
| | 1050 | 226 | 4.65 | 948 | 208 | 4.56 |
| | 820 | 192 | 4.27 | 925 | 227 | 4.07 |
| AVG | 900 | 203 | 4.44 | 934 | 217 | 4.31 |

TABLE 10B

| | CONTROL | TREATED | Difference |
|---|---|---|---|
| Lbs lint/ac | 1006 | 1047 | 41 |
| Bales/ac | 2.1 | 2.2 | 4% |

Cotton plants treated with HYTa and 18-0-0-3S yielded an increase of about 41-340 lbs of lint per acre as compared to plots treated with 18-0-0-3S alone.

The invention claimed is:

1. A process comprising contacting soil, seed, seedling, or plant foliage with a composition comprising the microbes in HYTa (ATCC Patent Deposit Designation PTA-10973) and liquid fertilizer.

2. The process of claim 1, wherein said microbial composition is activated.

3. The process of claim 1, wherein said microbial composition is activated by incubation in said liquid fertilizer prior to said contacting.

4. The process of claim 3, wherein said incubation is for 24 to 168 hours prior to said contacting.

5. The process of claim 1, wherein said contacting is of said soil to form treated soil.

6. The process of claim 1, wherein said liquid fertilizer comprises soluble nitrogen.

7. The process of claim 6, wherein said soluble nitrogen comprises an organic soluble nitrogen source or a nitrogen-containing inorganic salt.

8. The process of claim 7, wherein said nitrogen-containing inorganic salt comprises ammonium hydroxide, ammonium nitrate, ammonium sulfate, ammonium pyrophosphate, ammonium thiosulfate, or combinations thereof.

9. The process of claim 7, wherein said organic soluble nitrogen source comprises urea.

10. The process of claim 1, further comprising contacting the soil, seed, seedling, or plant foliage with HYTb and/or HYTd, wherein said HYTb is the liquid fraction obtained from the fermentation of chitin-containing organisms by HQE (ATCC Patent Deposit Designation PTA-10861) and said HYTd is the liquid fraction obtained from the fermentation of chitin in HYTb by HQE.

11. The process of claim 1, further comprising contacting the soil, seed, seedling, or plant foliage with HYTc, wherein said HYTc is the solid fraction obtained from the fermentation of chitin-containing organisms with HQE (ATCC Patent Deposit Designation PTA-10861).

12. The process of claim 1, further comprising contacting the soil, seed, seedling, or plant foliage with (i) HYTb and/or HYTd and (ii) HYTc, wherein said HYTb is the liquid fraction obtained from the fermentation of chitin-containing organisms with HQE (ATCC Patent Deposit Designation PTA-10861), said HYTc is the solid fraction obtained from the fermentation of chitin-containing organisms with HQE (ATCC Patent Deposit Designation PTA-10861), and said HYTd is the liquid fraction obtained from the fermentation of chitin in HYTb by HQE.

* * * * *